United States Patent
Yamamoto et al.

(10) Patent No.: US 10,757,301 B2
(45) Date of Patent: Aug. 25, 2020

(54) IMAGE PICKUP MODULE AND ENDOSCOPE

(71) Applicant: OLYMPUS CORPORATION, Tokyo (JP)

(72) Inventors: Ken Yamamoto, Tokyo (JP); Takuro Suyama, Tokyo (JP); Takahiro Shimohata, Tokyo (JP); Takatoshi Igarashi, Tokyo (JP); Hiroshi Kobayashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/403,782

(22) Filed: May 6, 2019

(65) Prior Publication Data

US 2019/0260917 A1 Aug. 22, 2019

Related U.S. Application Data

(63) Continuation of application No. PCT/JP2016/083451, filed on Nov. 11, 2016.

(51) Int. Cl.
*A61B 1/04* (2006.01)
*H04N 5/225* (2006.01)
*A61B 1/05* (2006.01)
*H01L 27/146* (2006.01)
*H01L 25/065* (2006.01)
(Continued)

(52) U.S. Cl.
CPC .......... *H04N 5/2252* (2013.01); *A61B 1/04* (2013.01); *A61B 1/051* (2013.01); *H01L 25/065* (2013.01); *H01L 25/07* (2013.01); *H01L 25/18* (2013.01); *H01L 27/14* (2013.01);
(Continued)

(58) Field of Classification Search
None
See application file for complete search history.

(56) References Cited

U.S. PATENT DOCUMENTS

2013/0070072 A1* 3/2013 Honda ............... A61B 1/00096
348/76
2015/0281539 A1* 10/2015 Ueki ...................... H04N 5/232
348/298

FOREIGN PATENT DOCUMENTS

JP 2001-104247 A 4/2001
JP 2005-334509 A 12/2005
(Continued)

OTHER PUBLICATIONS

International Search Report dated Dec. 27, 2016 issued in PCT/JP2016/083451.

*Primary Examiner* — Eileen M Adams
(74) *Attorney, Agent, or Firm* — Scully, Scott, Murphy & Presser, P.C.

(57) ABSTRACT

An image pickup module including: an image pickup unit having a plurality of stacked semiconductor devices, the plurality of stacked semiconductor devices including an image pickup sensor; and a frame including a hollow portion in which the image pickup unit is inserted, wherein the image pickup unit includes a first side surface orthogonal to a principal surface of the image pickup sensor, and a second side surface opposed to the first side surface, and two edges of four edges defining the first side surface of the image pickup unit are in contact with an inner surface of the frame, the two edges being orthogonal to the principal surface of the image pickup device, and the second side surface is not in contact with the inner surface of the frame.

20 Claims, 6 Drawing Sheets

(51) Int. Cl.
*H01L 25/18* (2006.01)
*H04N 5/369* (2011.01)
*H01L 27/14* (2006.01)
*H01L 25/07* (2006.01)

(52) U.S. Cl.
CPC ..... *H01L 27/14634* (2013.01); *H04N 5/2253* (2013.01); *H04N 5/369* (2013.01); *H04N 2005/2255* (2013.01)

(56) References Cited

FOREIGN PATENT DOCUMENTS

WO   WO 2013/179766 A1   12/2013
WO   WO 2014/174994 A1   10/2014

\* cited by examiner

IMAGE PICKUP MODULE AND ENDOSCOPE

CROSS REFERENCE TO RELATED APPLICATION

This application is a continuation application of PCT/JP2016/083451 filed on Nov. 11, 2016, the entire contents of which are incorporated herein by this reference.

BACKGROUND

1. Field

Embodiments relate to an image pickup module that acquires an image, and an endoscope including the image pickup module.

2. Description of the Related Art

An endoscope acquires an image in a body of a patient by inserting an insertion portion including, in a distal end portion thereof, an image pickup module into the body of the patient, for example. Japanese Patent Application Laid-Open Publication No. 2005-334509 discloses an image pickup unit including an image pickup device on which a light-receiving portion is formed and a wiring board bonded to the rear surface of the image pickup device.

In the image pickup unit, chip components such as a capacitor, resistor, and IC chips that constitute a driving circuit of the image pickup device are mounted on the wiring board. Therefore, a length in the optical axis direction of the image pickup unit is long.

In recent years, a semiconductor device provided with a planar device (thin film device) having functions of electronic components such as a capacitor, and the like has been developed. The length of the image pickup unit can be shortened by bonding a device stacked body in which a plurality of semiconductor devices are stacked to the rear surface of the image pickup device. An endoscope including a short and small image pickup unit is low-invasive, since a length of a distal end rigid portion is short.

SUMMARY OF THE INVENTION

Accordingly, an image pickup module is provided. The image pickup module comprising: an image pickup unit having a plurality of stacked semiconductor devices, the plurality of stacked semiconductor devices including an image pickup sensor; and a frame including a hollow portion in which the image pickup unit is inserted, wherein the image pickup unit includes a first side surface orthogonal to a principal surface of the image pickup sensor, and a second side surface opposed to the first side surface, and two edges of four edges defining the first side surface of the image pickup unit are in contact with an inner surface of the frame, the two edges being orthogonal to the principal surface of the image pickup device, and the second side surface is not in contact with the inner surface of the frame.

The image pickup unit can have a cuboid shape, the image pickup unit includes a third side surface and a fourth side surface, each of the third and fourth side surfaces being orthogonal to the first side surface, the inner surface of the frame can have a rectangular-shaped cross section, the inner surface including a first inner surface, a second inner surface opposed to the first inner surface, and a third inner surface and a fourth inner surface, each of the third and fourth inner surfaces being orthogonal to the first inner surface, the first side surface is in contact with the first inner surface, and the third side surface is in contact with the third inner surface, and the second side surface is not in contact with the second inner surface, and the fourth side surface is not in contact with the fourth inner surface. The image pickup module can further comprise a resin filling a gap between the second side surface and the second inner surface and filling a gap between the fourth side surface and the fourth inner surface, and the resin is not disposed on at least a part of a contact surface between the first side surface and the first inner surface and at least a part of a contact surface between the third side surface and the third inner surface. The image pickup unit can include a recessed portion on the first side surface, and the frame includes, on the first inner surface, a protruding portion that is in contact with the recessed portion. The image pickup unit can include a protruding portion on the first side surface and the frame includes, on the first inner surface, a recessed portion in which the protruding portion is housed.

The inner surface of the frame can have a circular-shaped cross section.

A longitudinal axis of the image pickup unit can be parallel to a longitudinal axis of the frame.

Also provided is an endoscope comprising: an insertion portion having a distal end portion; and an image pickup module disposed in the distal end portion of the insertion portion, the image pickup module comprising: an image pickup unit having a plurality of stacked semiconductor devices including an image pickup sensor; and a frame including a hollow portion in which the image pickup unit is inserted, wherein the image pickup unit includes a first side surface orthogonal to a principal surface of the image pickup sensor and a second side surface opposed to the first side surface, and two edges of four edges defining the first side surface of the image pickup unit are in contact with an inner surface of the frame, the two edges being orthogonal to the principal surface of the image pickup device, and the second side surface is not in contact with the inner surface of the frame.

The frame can be a rigid member disposed the distal end portion, and the hollow portion can be a through hole of the rigid member.

A longitudinal axis of the image pickup unit can be parallel to a longitudinal axis of the frame.

Still further provided is an insertion portion for use with an endoscope, the insertion portion comprising: a distal end portion; and an image pickup module disposed in the distal end portion of the insertion portion, the image pickup module comprising: an image pickup unit having a plurality of stacked semiconductor devices including an image pickup sensor; and a frame including a hollow portion in which the image pickup unit is inserted, wherein the image pickup unit includes a first side surface orthogonal to a principal surface of the image pickup sensor and a second side surface opposed to the first side surface, and two edges of four edges defining the first side surface of the image pickup unit are in contact with an inner surface of the frame, the two edges being orthogonal to the principal surface of the image pickup device, and the second side surface is not in contact with the inner surface of the frame.

A longitudinal axis of the image pickup unit can be parallel to a longitudinal axis of the frame.

DETAILED DESCRIPTION OF THE PREFERRED EMBODIMENT(S)

<First Embodiment>

Figure 1:
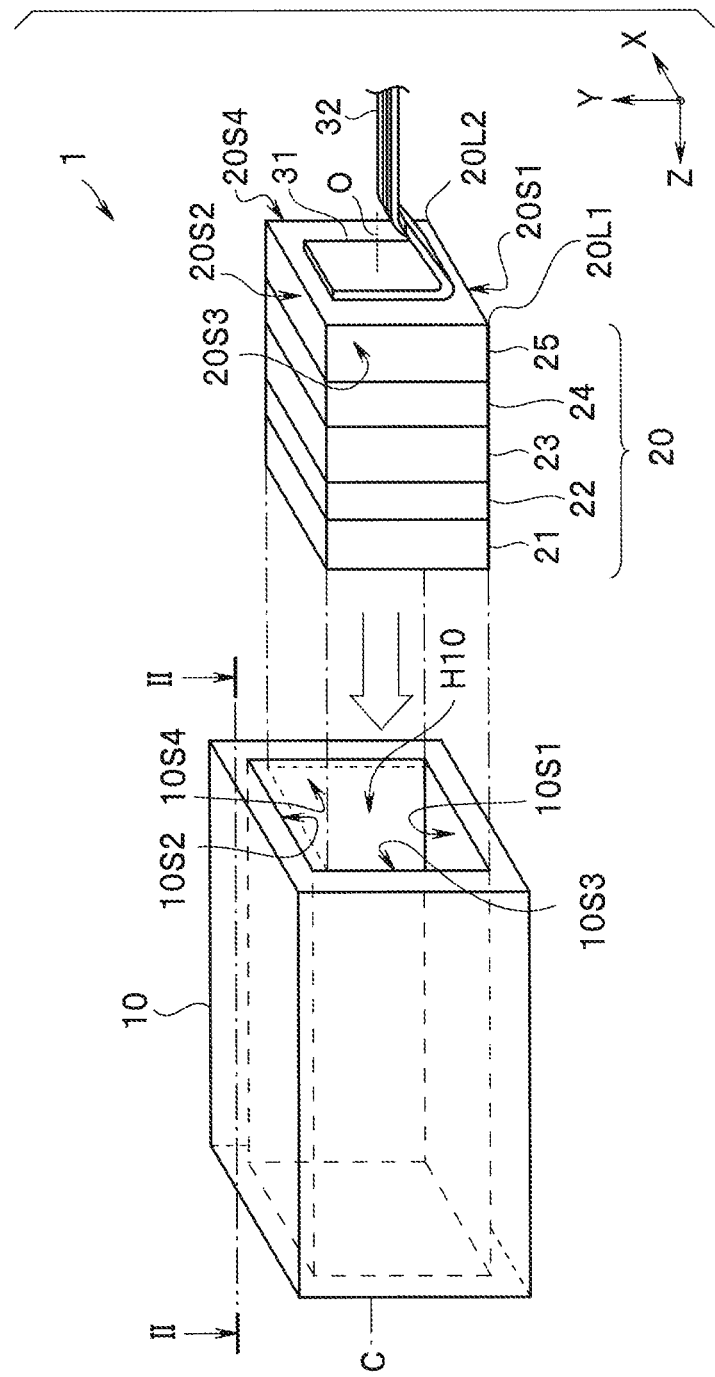
FIG. 1 is an exploded perspective view of an image pickup module according to a first embodiment.
Figure 2:
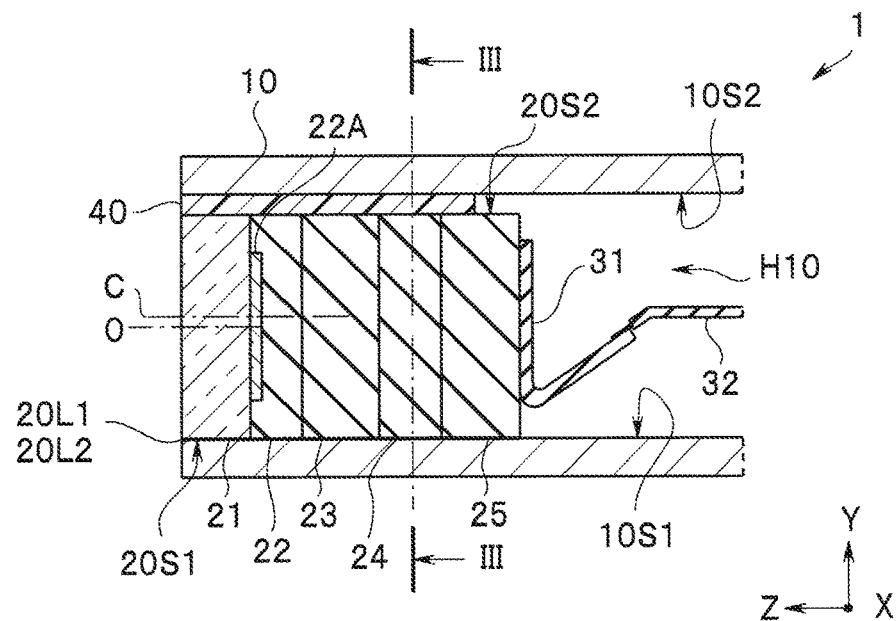
FIG. 2 is a cross-sectional view of the image pickup module according to the first embodiment, which is taken along the line II-II in FIG. 1.
Figure 3:
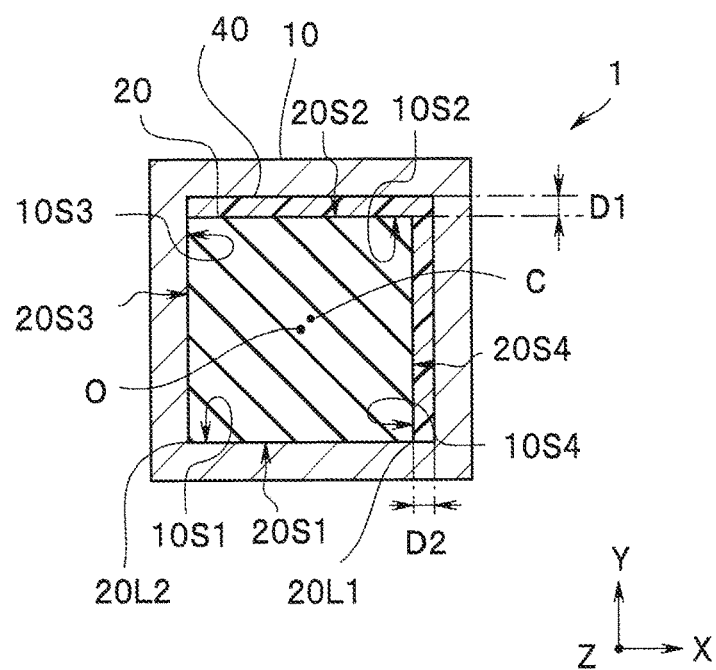
FIG. 3 is a cross-sectional view of the image pickup module according to the first embodiment, which is taken along the line III-III in FIG. 2.

As shown in FIGS. 1 to 3, an image pickup module 1 according to the present embodiment includes a frame member 10 which is a housing, and an image pickup unit 20 that is inserted in a hollow portion H10 of the frame member 10.

In the description below, each of the drawings based on each of the embodiments is a pattern diagram, and care should be taken to the fact that the relationship between the thicknesses and widths of the respective parts, a ratio of the thicknesses, relative angles, and the like of the parts are different from the actual ones, and there is a case where the respective drawings include the parts in which the relationships and ratios among the dimensions are different from those in other drawings. There is a case where illustration of some constituent elements is omitted.

In addition, with regard to an optical axis (O) direction, a direction in which an image pickup device 22 is arranged (Z-axis value increasing direction) is referred to as "front" and a direction in which a signal cable 32 is arranged (Z-axis value decreasing direction) is referred to as "rear".

Note that the image pickup module 1 further includes a wiring board 31 bonded to a rear end surface of the image pickup unit 20, and a signal cable 32 bonded to the wiring board 31. Note that the signal cable 32 may be directly bonded to the rear end surface of the image pickup unit 20.

The image pickup unit 20 is a stack including a cover glass 21, an image pickup device 22 (an image sensor) which is a first semiconductor device, and a plurality of semiconductor devices 23, 24, and 25. In other words, the image pickup unit 20 is formed by stacking the plurality of semiconductor devices 22 to 25 including the image pickup device 22.

The image pickup device 22 has a rectangular shape in a planar view, that is, the cross-sectional shape of the image pickup device in the direction orthogonal to the optical axis O is rectangular. The image pickup device 22 is provided with a light-receiving portion 22A that receives light of an object image, which is incident through the cover glass 21, and converts the received light into an electric signal. The light-receiving portion 22A is a CCD or a CMOS light-receiving device, and the like, and configured to receive light and generate an electric signal by performing photoelectric conversion on the received light. The light-receiving portion 22A is connected to an electrode on the rear surface of the image pickup device 22 through a through-wiring.

The semiconductor devices 23 to 25 perform primary processing on the electric signal outputted from the image pickup device 22. Each of the semiconductor devices 23 to 25, which has a rectangular shape in a planar view, includes a planar device constituting electronic component functional circuits such as a capacitor, a resistor, or a buffer, or a processing circuit such as a noise removing circuit or an analog-digital conversion circuit.

Each of the semiconductor devices 23 to 25 may have a different thickness. In addition, the planar device of each of the semiconductor devices 23 to 25 may be formed on one side or both sides of each of the semiconductor devices. Furthermore, the stacking number of the semiconductor devices has only to be two or more, and is not limited to three as disclosed in the present embodiment.

The image pickup device 22 and the semiconductor devices 23 to 25 are stacked through sealing resin (not shown). The sealing resin is an epoxy resin, an acrylic resin, a polyimide resin, a silicone resin, a polyvinyl resin, or the like. That is, the semiconductor devices 23 to 25 are connected to each other through a through-wiring and a bump, similarly as the image pickup device 22.

The image pickup unit 20 is a cuboidal wafer-level stack, as will be described later. More specifically, the image pickup unit 20 is fabricated by cutting a bonded wafer 20W formed by stacking a glass wafer 21W including a plurality of cover glasses 21, an image pickup wafer 22W including a plurality of image pickup devices 22, and the semiconductor wafers 23W to 25W including a plurality of semiconductor devices 23 to 25, respectively (see FIG. 7).

Therefore, the outer dimensions in the direction orthogonal to the optical axis (planar view sizes) of the cover glass 21, the image pickup device 22, and the semiconductor devices 23 to 25 are the same. The cover glass 21 and the semiconductor devices 23 to 25, which are projected on a projection surface in the direction orthogonal to the optical axis, are arranged within a projection surface of the image pickup device 22.

The image pickup unit 20, which is a wafer-level stack, is an extremely small unit, the planar view size (cross-sectional dimension in the direction orthogonal to the optical axis) of which is equal to or smaller than 2 millimeters square, for example.

The image pickup unit 20 is short and small, since the image pickup unit includes a device stacked body. In addition, the outer dimension of the image pickup unit 20 in the direction orthogonal to the optical axis is small, since the planar view size of the image pickup unit 20 is the same as that of the image pickup device 22.

The cuboidal image pickup unit 20 includes a rectangular first side surface 20S1, a second side surface 20S2 opposed to the first side surface 20S1, a third side surface 20S3 and the fourth side surface 20S4 that are orthogonal to the first side surface 20S1 and the second side surface 20S2. The first side surface 20S1 and the second side surface 20S2 are orthogonal to the image pickup device surface which is a principal surface of the image pickup device 22.

On the other hand, the frame member 10 having the hollow portion H10 in which the image pickup unit 20 is inserted is made of a metal material such as SUS (stainless steel). The frame member 10 has the hollow portion H10, which is a through hole, has an inner surface whose cross-sectional shape is rectangular. In the image pickup unit 20, the central axis C of the hollow portion H10 is the same as the central axis C of the frame member 10.

The hollow portion H10 includes an inner surface composed of a first inner surface 10S1, a second inner surface 10S2 opposed to the first inner surface 10S1, and a third inner surface 10S3 and a fourth inner surface 10S4 orthogonal to the first inner surface 10S1 and the second inner surface 10S2.

The outer dimension of the image pickup unit 20 in the direction orthogonal to the optical axis is smaller than an inner dimension of the hollow portion H10 of the frame member 10 in the direction orthogonal to the optical axis. Only the two side surfaces 20S1, 20S3, which are orthogonal to each other, of the image pickup unit 20 are in contact respectively with the inner surfaces 10S1, 10S3 of the frame member 10. That is, gaps respectively having the lengths D1, D2 are formed respectively between the second side surface 20S2 and the second inner surface 10S2 and between the fourth side surface 20S4 and the fourth inner surface 10S4, and the gaps are filled with resin 40.

In other words, in the image pickup module 1, two long edges 20L1, 20L2, which are orthogonal to the image pickup device surface, of the four edges defining the rectangular first side surface 20S1 of the image pickup unit 20 are in contact with the inner surface of the frame member 10 and the second side surface 20S2 is not in contact with the inner surface of the frame member 10. The first side surface 20S1 of the image pickup unit 20 is in contact with the first inner surface 10S1 of the frame member 10, and the third side surface 20S3 is in contact with the third inner surface 10S3, but the second side surface 20S2 is not in contact with the second inner surface 10S2, and the fourth side surface 20S4 is not in contact with the fourth inner surface 10S4, either.

Note that, in the image pickup module 1, it is the long edges of the first side surface 20S1 that are in contact with the inner surface of the frame member 10. However, it is needless to say that there is a case where not the long edges but the short edges of the image pickup unit 20 are in contact with the inner surface of the frame member, depending on the shape of the image pickup unit 20.

When the differences D1, D2 between the outer dimension of the image pickup unit 20 and the inner dimension of the hollow portion H10 of the frame member 10 are small, insertion of the image pickup unit 20 into the hollow portion H10 is not easy. On the other hand, when the differences D1, D2 are large, there is a possibility that the optical axis O and the central axis C are not in parallel with each other.

However, in the image pickup module 1, the two surfaces 20S1, 20S3 of the image pickup unit 20 are in contact respectively with the two surfaces 10S1, 10S3 of the hollow portion H10 of the frame member 10, without another member (for example, the resin 40) being interposed. Therefore, the optical axis O of the image pickup unit 20 and the central axis C of the hollow portion H10 of the frame member 10 are parallel with each other, precisely.

Note that, when the gaps are filled with the resin 40, there is a case where the resin 40 unavoidably intrudes into the contact surfaces due to the surface tension of the resin. However, in the image pickup module 1, the resin 40 is not present on at least a part of the contact surfaces. Therefore, it can be judged that the image pickup unit and the frame member are fixed to each other by the resin 40, with the two side surfaces 20S1, 20S3 and the two inner surfaces 10S1, 10S3 being in contact with each other, respectively.

Specifically, in the image pickup module 1, the resin 40 is not present on at least a part of the contact surface between the first side surface 20S1 and the first inner surface 10S1 and at least a part of the contact surface between the third side surface 20S3 and the third inner surface 10S3.

Manufacturing of the image pickup module 1 is improved, since the optical axis O of the image pickup unit 20 and the central axis C of the hollow portion H10 of the frame member 10 are positioned so as to be in parallel with each other precisely.

Note that, even when only the first side surface 20S1 and the first inner surface 10S1 are in contact with each other, and the third side surface 20S3 and the third inner surface 10S3 are not in contact with each other, for example, the optical axis direction (Z axis) and one direction (Y axis) orthogonal to the optical axis of the three axes (XYZ) are positioned, which results in easier manufacturing compared with the case where none of the side surfaces is in contact with the inner surface.

Furthermore, the frame member 10 made of metal having high heat conductivity and the image pickup unit 20 are in contact with each other not through another member, which enables the heat generated by the image pickup unit 20 to be effectively transferred to the frame member 10. For example, the image pickup signal outputted from the image pickup device 22 is not likely to be influenced by thermal noise and the like, which enables the image pickup signal to be stable. The frame member 10 can be made of a material having heat conductivity of 10 W/(mk) or more, in order to obtain a noticeable heat radiation effect. The heat conductivity of SUS is 20 W/(mk), for example.

<Modified Examples of First Embodiment>

Image pickup modules 1A, 1B according to the modified examples are similar to the image pickup module 1 and have the same effects as those of the image pickup module 1. Therefore, the constituent elements having the same functions as those of the constituent elements in the image pickup module 1 are attached with the same reference signs and descriptions thereof will be omitted.

<First Modified Example of First Embodiment>

Figure 4:
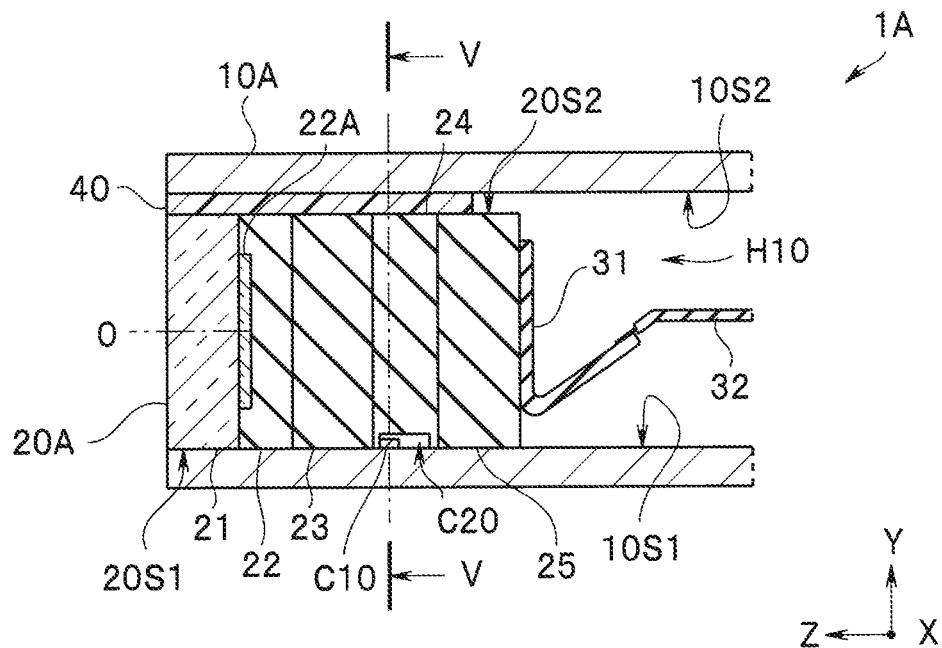
FIG. 4 is a cross-sectional view of an image pickup module according to a first modified example of the first embodiment.
Figure 5:
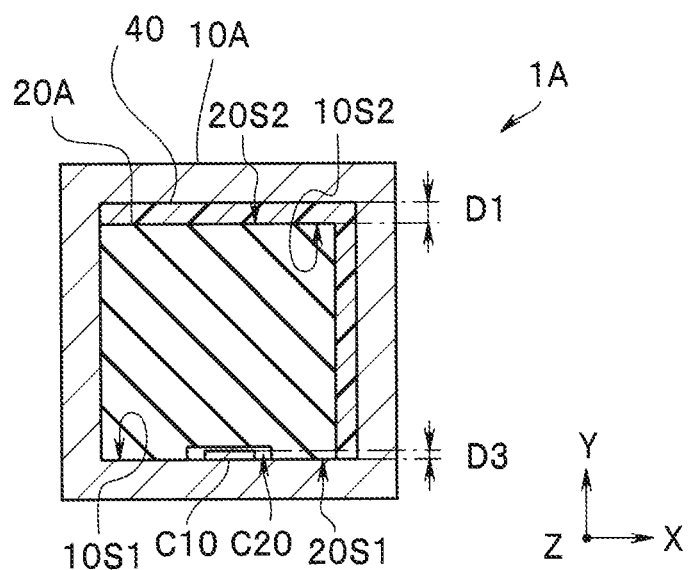
FIG. 5 is a cross-sectional view of the image pickup module according to the first modified example of the first embodiment, which is taken along the line V-V in FIG. 4.

As shown in FIGS. 4 and 5, the image pickup module 1A according to the first modified example includes a recessed portion C20 on a first side surface 20S1 of an image pickup unit 20A, and a protruding portion C10, which is in contact with the recessed portion C20, formed on a first inner surface 10S1 of a frame member 10A. The height D3 of the protruding portion C10 is smaller than a length D1 of a gap between the image pickup unit 20A and the frame member 10A.

Note that the protruding portion C10 may be a part of the frame member 10A, or may be another member which is separate from the frame member 10A. For example, the protruding portion C10 may be inserted into a through hole formed on the side surface of the frame member 10A.

In the image pickup module 1A, the distal end surface of the protruding portion C10 and the inner surface of the recessed portion C20 are in contact with each other, which specifies the position of the image pickup unit 20A in the hollow portion H10 in the optical axis direction (Z axis direction). In addition, the recessed portion C20 serves as a receiver of the resin 40 intruded onto the contact surface, which provides an effect of reducing the amount of resin 40 to be remained on the contact surface.

With the image pickup module 1A, the positioning of the image pickup unit 20A in the optical axis direction with respect to the frame member 10A is improved.

<Second Modified Example of First Embodiment>

Figure 6:
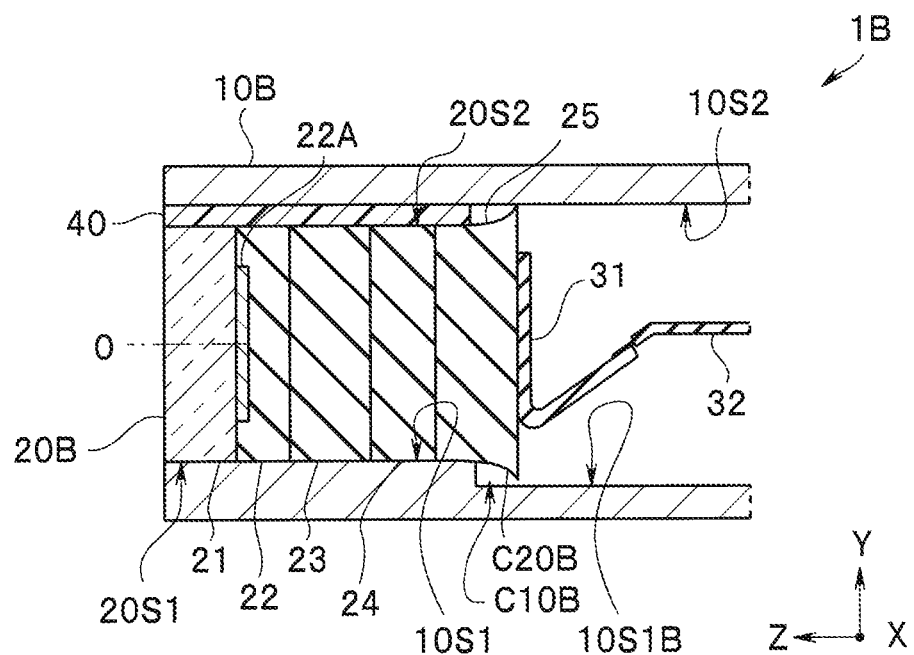
FIG. 6 is a cross-sectional view of an image pickup module according to a second modified example of the first embodiment.

As shown in FIG. 6, the image pickup module 1B according to the second modified example includes a recessed portion C10B on a first inner surface 10S1 of the frame member 10B. Although a protruding portion C20B is formed on a first side surface 20S1 of the image pickup unit 20B, the protruding portion C20B is housed in the recessed portion 10S1B of the frame member. Therefore, the protruding portion C20B of the image pickup unit 20B is not in contact with an inner surface 10SB1 of the frame member 10B.

Figure 7:
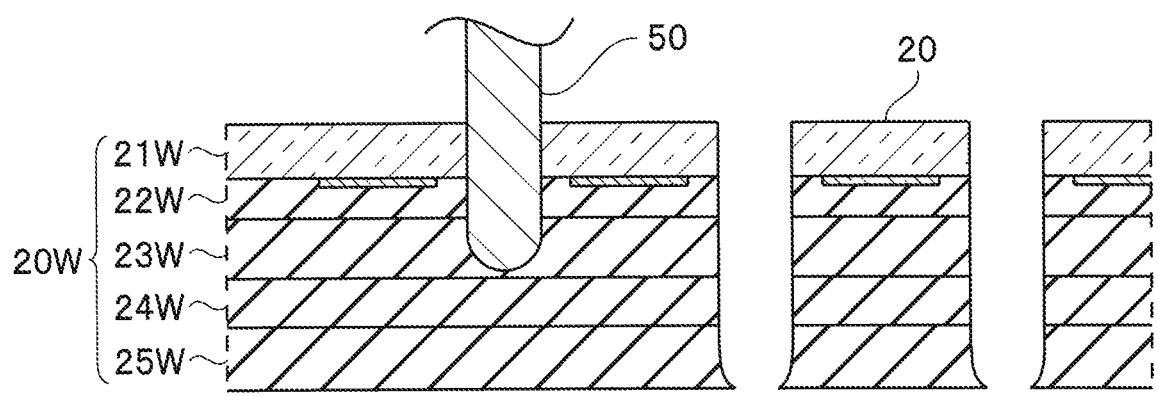
FIG. 7 is a cross-sectional view for describing a manufacturing method of the image pickup module according to the second modified example of the first embodiment.

Note that the protruding portion C20B of the image pickup unit 20B is formed when the bonded wafer 20W including a plurality of image pickup units 20B is cut by using a dicing blade 50, as shown in FIG. 7, for example. Therefore, manufacturing of the image pickup unit 20B is improved.

<Second Embodiment>

An image pickup module 1C according to the present embodiment is similar to the image pickup module 1 and have the same effects as those of the image pickup module 1. Therefore, the constituent elements having the same functions as those of the constituent elements in the image pickup module 1 are attached with the same reference signs and descriptions thereof will be omitted.

Figure 8:
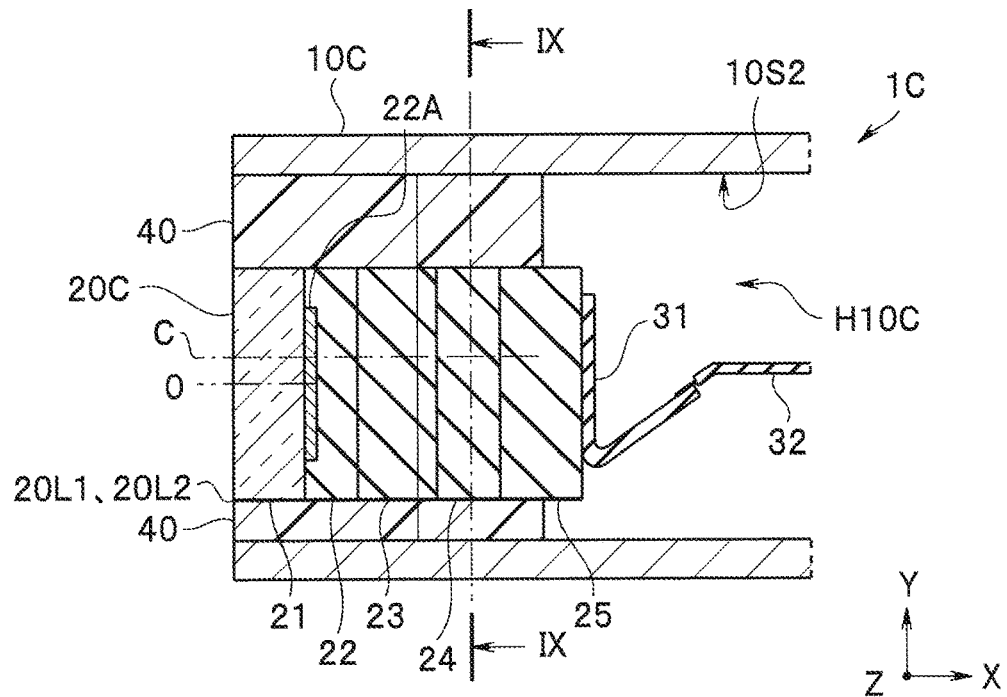
FIG. 8 is a cross-sectional view of an image pickup module according to a second embodiment.
Figure 9:
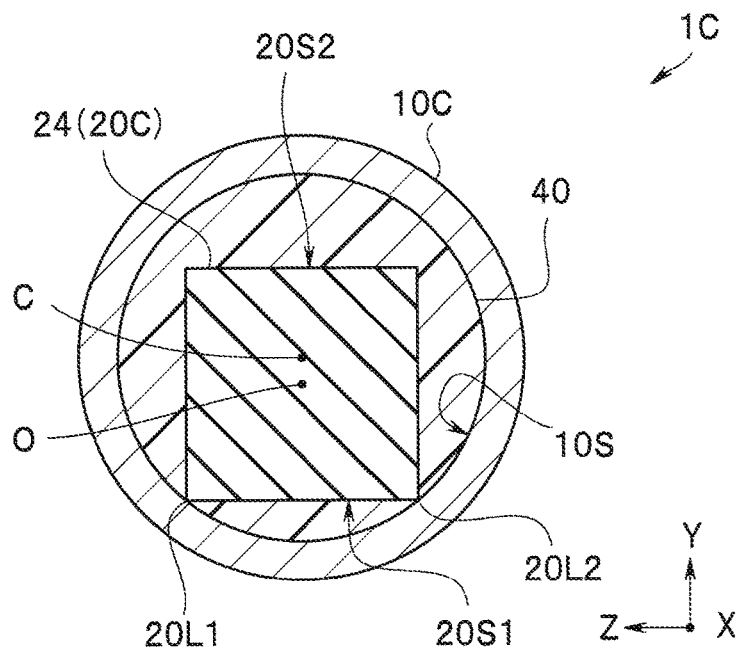
FIG. 9 is a cross-sectional view of the image pickup module according to the second embodiment, which is taken along the line IX-IX in FIG. 8.

As shown in FIGS. 8 and 9, a frame member 10C of the image pickup module 1C has a hollow portion H10C having an inner surface whose cross-sectional shape is circular.

Two long edges 20L1, 20L2 of a rectangular first side surface 20S1 of an image pickup unit 20C are in contact with an inner surface 10S of the frame member 10C, and a second side surface 20S2 is not in contact with the inner surface 10S.

Note that each of the image pickup units 20, 20A to 20C is a cuboid, the cross-sectional shape of which in the direction orthogonal to the optical axis is rectangular. However, the image pickup unit may have a cross section of a polygonal shape such as a hexagonal shape, for example. In addition, chamfering processing or curve processing may be performed on the corners of the long edges of the cuboid. For example, the image pickup unit subjected to the chamfering processing is insertable into a frame member whose inner dimension is small, and another member can be inserted in a gap between the image pickup unit and the frame member.

<Third Embodiment>

Next, description will be made on an endoscope 9 according to the third embodiment.

Figure 10:
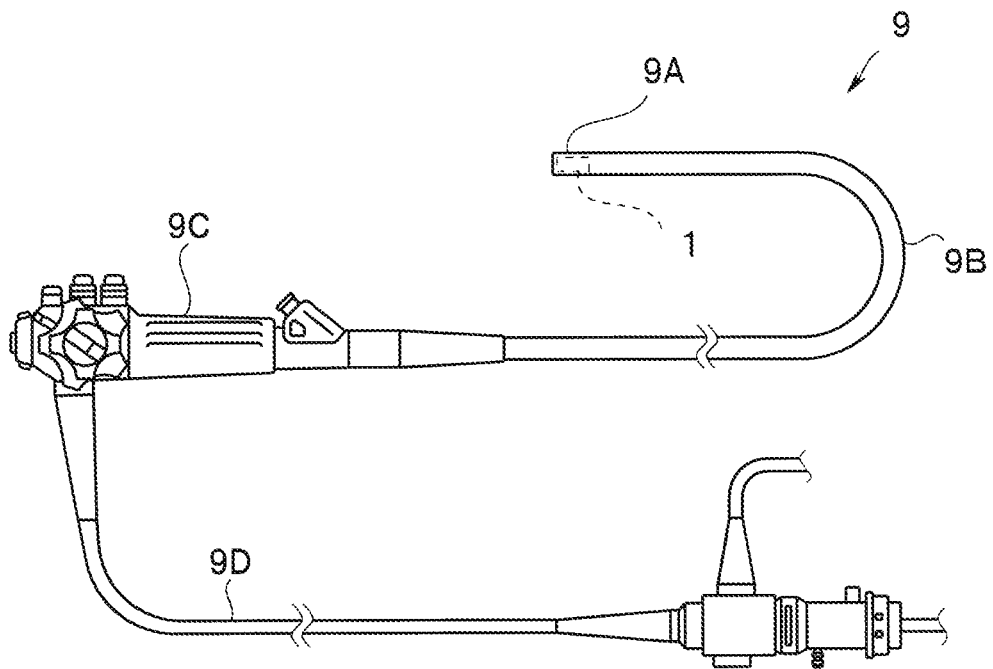
FIG. 10 is a perspective view of an endoscope according to a third embodiment.

As shown in FIG. 10, the endoscope 9 includes: an insertion portion 9B which includes, at a distal end portion 9A, the image pickup module 1; an operation portion 9C disposed on the proximal end side of the insertion portion 9B; and a universal cord 9D extended from the operation portion 9C. The universal cord 9D is connected with the signal cable 32 of the image pickup module 1.

The image pickup unit inserted in the frame member is inserted in the through hole of the distal end portion 9A.

The endoscope 9 includes the image pickup module 1, manufacturing of which is improved. Therefore, manufacturing of the endoscope 9 is improved.

Figure 11:
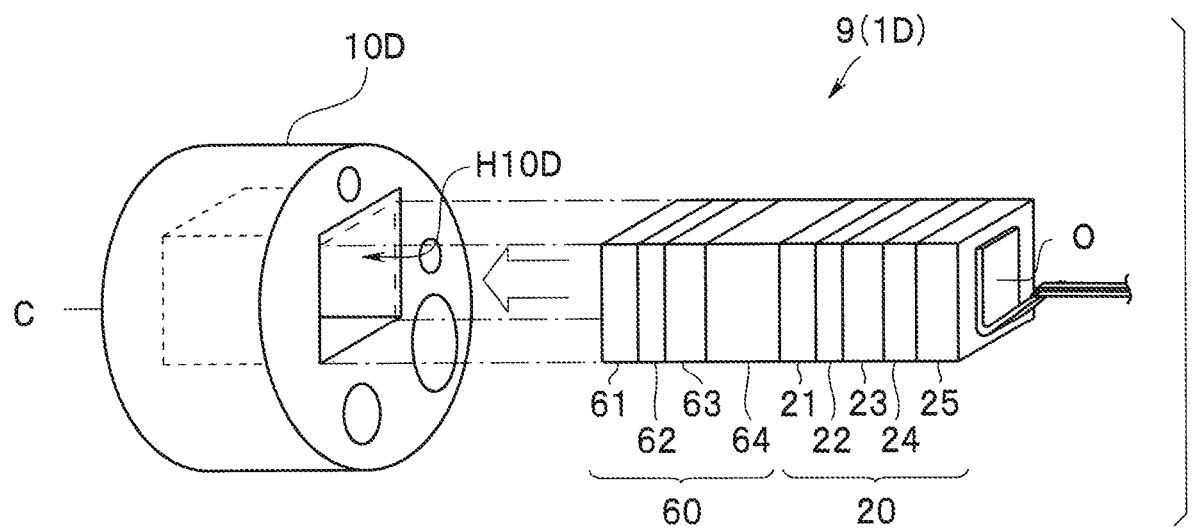
FIG. 11 is an exploded view of a distal end portion of the endoscope according to the third embodiment.

Note that, as shown in FIG. 11, the image pickup unit 20 of the image pickup module 1 may include an optical unit 60 in which a plurality of optical devices 61 to 63 are stacked on the front surface of the cover glass 21.

For example, the cuboidal optical unit 60 is fabricated by cutting a bonded optical wafer formed by bonding a plurality of optical wafers each including the plurality of optical devices 61 to 64. The optical devices 61 to 64 are a concave lens, a convex lens, a spacer, or a filter, for example.

In addition, a camera unit including the optical unit 60 and the image pickup unit 20 may be fabricated by cutting a bonded unit wafer formed by bonding a plurality of optical wafers to an image pickup wafer 22W, and the like. The wafer-level camera unit is a cuboid and has a small outer dimension in the direction orthogonal to the optical axis.

Furthermore, as shown in FIG. 11, a frame member 10D in which an image pickup module 1D is inserted may be a rigid member that constitutes the distal end portion of the endoscope 9. That is, the through hole of the rigid member may be a hollow portion H10D.

Note that it is needless to say that the endoscope including each of the image pickup modules 1A to 1C has the effect of the endoscope 9, and has the effect of each of the image pickup modules 1A to 1C. In addition, the endoscope is not limited to a medical endoscope, but may be an industrial endoscope.

The present invention is not limited to the above-described embodiments and the modified examples, and various changes and modifications are possible in a range without changing the gist of the present invention.

What is claimed is:

1. An image pickup module comprising:
   an image pickup unit having a plurality of stacked semiconductor devices, the plurality of stacked semiconductor devices including an image pickup sensor, the image pickup sensor having a light receiving surface orthogonal to an optical axis of the image pickup unit; and
   a frame including a hollow portion in which the image pickup unit is inserted,
   wherein the image pickup unit includes a first side surface orthogonal to the light receiving surface of the image pickup sensor, the image pickup unit further including a second side surface opposed to the first side surface, and
   two edges of four edges defining the first side surface of the image pickup unit are in contact with an inner surface of the frame, the two edges being orthogonal to the light receiving surface of the image pickup sensor, and the second side surface is not in contact with the inner surface of the frame.

2. The image pickup module according to claim 1, wherein
   the image pickup unit has a cuboid shape, the image pickup unit includes a third side surface and a fourth side surface, each of the third and fourth side surfaces being orthogonal to the first side surface,
   the inner surface of the frame has a rectangular-shaped cross section, the inner surface including a first inner surface, a second inner surface opposed to the first inner surface, and a third inner surface and a fourth inner surface, each of the third and fourth inner surfaces being orthogonal to the first inner surface,
   the first side surface is in contact with the first inner surface, and the third side surface is in contact with the third inner surface, and
   the second side surface is not in contact with the second inner surface, and the fourth side surface is not in contact with the fourth inner surface.

3. The image pickup module according to claim 2, further comprising a resin filling a gap between the second side surface and the second inner surface and filling a gap between the fourth side surface and the fourth inner surface, and the resin is not disposed on at least a part of a contact surface between the first side surface and the first inner surface and at least a part of a contact surface between the third side surface and the third inner surface.

4. The image pickup module according to claim 2, wherein the image pickup unit includes a recessed portion on the first side surface, and the frame includes, on the first inner surface, a protruding portion that is in contact with the recessed portion.

5. The image pickup module according to claim 2, wherein the image pickup unit includes a protruding portion on the first side surface and the frame includes, on the first inner surface, a recessed portion in which the protruding portion is housed.

6. The image pickup module according to claim 1, wherein the inner surface of the frame has a circular-shaped cross section.

7. The image pickup module according to claim 1, wherein a longitudinal axis of the image pickup unit is parallel to a longitudinal axis of the frame.

8. An endoscope comprising:

an insertion portion having a distal end portion; and an image pickup module disposed in the distal end portion of the insertion portion, the image pickup module comprising:

an image pickup unit having a plurality of stacked semiconductor devices including an image pickup sensor, the image pickup sensor having a light receiving surface orthogonal to an optical axis of the image pickup unit; and a frame including a hollow portion in which the image pickup unit is inserted, wherein the image pickup unit includes a first side surface orthogonal to the light receiving surface of the image pickup sensor, the image pickup unit further including a second side surface opposed to the first side surface, and two edges of four edges defining the first side surface of the image pickup unit are in contact with an inner surface of the frame, the two edges being orthogonal to the light receiving surface of the image pickup sensor, and the second side surface is not in contact with the inner surface of the frame.

9. The endoscope according to claim 8, wherein the frame is a rigid member disposed the distal end portion, and the hollow portion is a through hole of the rigid member.

10. The endoscope according to claim 8, wherein a longitudinal axis of the image pickup unit is parallel to a longitudinal axis of the frame.

11. An insertion portion for use with an endoscope, the insertion portion comprising:

a distal end portion; and an image pickup module disposed in the distal end portion of the insertion portion, the image pickup module comprising:

an image pickup unit having a plurality of stacked semiconductor devices including an image pickup sensor, the image pickup sensor having a light receiving surface orthogonal to an optical axis of the image pickup unit; and a frame including a hollow portion in which the image pickup unit is inserted, wherein the image pickup unit includes a first side surface orthogonal to the light receiving surface of the image pickup sensor, the image pickup unit further including a second side surface opposed to the first side surface, and two edges of four edges defining the first side surface of the image pickup unit are in contact with an inner surface of the frame, the two edges being orthogonal to the light receiving surface of the image pickup sensor, and the second side surface is not in contact with the inner surface of the frame.

12. The insertion portion according to claim 11, wherein a longitudinal axis of the image pickup unit is parallel to a longitudinal axis of the frame.

13. The insertion portion according to claim 11, wherein the image pickup unit has a cuboid shape, the image pickup unit includes a third side surface and a fourth side surface, each of the third and fourth side surfaces being orthogonal to the first side surface, the inner surface of the frame has a rectangular-shaped cross section, the inner surface including a first inner surface, a second inner surface opposed to the first inner surface, and a third inner surface and a fourth inner surface, each of the third and fourth inner surfaces being orthogonal to the first inner surface, the first side surface is in contact with the first inner surface, and the third side surface is in contact with the third inner surface, and the second side surface is not in contact with the second inner surface, and the fourth side surface is not in contact with the fourth inner surface.

14. The insertion portion according to claim 13, further comprising a resin filling a gap between the second side surface and the second inner surface and filling a gap between the fourth side surface and the fourth inner surface, and the resin is not disposed on at least a part of a contact surface between the first side surface and the first inner surface and at least a part of a contact surface between the third side surface and the third inner surface.

15. The insertion portion according to claim 13, wherein the image pickup unit includes a recessed portion on the first side surface, and the frame includes, on the first inner surface, a protruding portion that is in contact with the recessed portion.

16. The insertion portion according to claim 13, wherein the image pickup unit includes a protruding portion on the first side surface and the frame includes, on the first inner surface, a recessed portion in which the protruding portion is housed.

17. The endoscope according to claim 8, wherein the image pickup unit has a cuboid shape, the image pickup unit includes a third side surface and a fourth side surface, each of the third and fourth side surfaces being orthogonal to the first side surface, the inner surface of the frame has a rectangular-shaped cross section, the inner surface including a first inner surface, a second inner surface opposed to the first inner surface, and a third inner surface and a fourth inner surface, each of the third and fourth inner surfaces being orthogonal to the first inner surface, the first side surface is in contact with the first inner surface, and the third side surface is in contact with the third inner surface, and the second side surface is not in contact with the second inner surface, and the fourth side surface is not in contact with the fourth inner surface.

18. The endoscope according to claim 17, further comprising a resin filling a gap between the second side surface and the second inner surface and filling a gap between the fourth side surface and the fourth inner surface, and the resin is not disposed on at least a part of a contact surface between the first side surface and the first inner surface and at least a part of a contact surface between the third side surface and the third inner surface.

19. The endoscope according to claim 17, wherein the image pickup unit includes a recessed portion on the first side surface, and the frame includes, on the first inner surface, a protruding portion that is in contact with the recessed portion.

20. The endoscope according to claim 17, wherein the image pickup unit includes a protruding portion on the first side surface and the frame includes, on the first inner surface, a recessed portion in which the protruding portion is housed.

\* \* \* \* \*